United States Patent [19]

Inoue et al.

[11] 4,150,288
[45] Apr. 17, 1979

[54] THICKNESS STANDARD SAMPLE AND METHOD OF CALIBRATING GAGE

[75] Inventors: Akira Inoue; Masanori Takahashi; Masao Kaneko, all of Tokyo, Japan

[73] Assignee: Kabushiki Kaisha Daini Seikosha, Japan

[21] Appl. No.: 787,440

[22] Filed: Apr. 14, 1977

[30] Foreign Application Priority Data

Apr. 14, 1976 [JP] Japan .............................. 51-46442[U]

[51] Int. Cl.² ............................................ G01N 23/22
[52] U.S. Cl. .................................. 250/252; 250/272; 428/344
[58] Field of Search ............... 250/252, 460, 272, 273; 428/653, 659, 606, 607, 344

[56] References Cited

U.S. PATENT DOCUMENTS

| 473,790 | 4/1892 | Sichel | 428/606 |
|---|---|---|---|
| 2,106,133 | 1/1938 | Goldman et al. | 428/344 |
| 2,654,684 | 10/1953 | Heikin | 428/344 |
| 2,804,416 | 8/1957 | Phillipsen | 428/344 |
| 3,938,125 | 2/1976 | Benassi | 428/653 |

*Primary Examiner*—Alfred E. Smith
*Assistant Examiner*—T. N. Grigsby
*Attorney, Agent, or Firm*—Robert E. Burns; Emmanuel J. Lobato; Bruce L. Adams

[57] ABSTRACT

A thickness standard sample consisting of a base plate and an even thick foil fixed on the base plate. The foil has a uniform standard thickness for calibrating an X-ray fluorescence thickness gauge or the like. The sample is very inexpensive and serves as an excellent uniform thickness standard sample so that an operator may set any point on the sample surface to the calibrating gauge axis.

8 Claims, 1 Drawing Figure

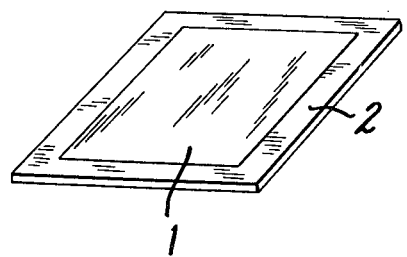

THICKNESS STANDARD SAMPLE AND METHOD OF CALIBRATING GAGE

BACKGROUND OF THE INVENTION

This invention relates to a thickness standard sample applicable to calibration of a thickness gauge using fluorescent X-ray or other radiant rays.

Prior thickness standard samples are formed with thin films electroplated or coated on base plates. These films are, for instance, 300 grams/m$^2$ of zinc in thickness and have thickness fluctuation of $\pm 50$ to 80 grams/m$^2$ in range in a sample of 100 mm $\times$ 200 mm surface area.

Because of this unevenness of the film thickness, they are not suitable for accurate calibration of industrial gauges such as X-ray thickness gauges.

BRIEF SUMMARY OF THE INVENTION

It is a principal object of this invention to provide a precise thickness standard sample having an even foil on a base plate.

BRIEF DESCRIPTION OF THE DRAWINGS

The drawing is a perspective view showing a thickness standard sample according to the invention.

DETAILED DESCRIPTION OF THE PREFERRED EMBODIMENT

A preferred embodiment of the invention will be described hereinafter with reference to the attached drawing, in which numeral 1 designates a foil with even thickness of, for instance, 10 to 50 $\mu$m and made of either metal (e.g. zinc or aluminium) or nonmetal, and numeral 2 designates a base plate which is made of either metal or nonmetal and as shown in the drawing is of greater thickness than the foil. Zinc foil is preferably selected for gauging the thickness of galvanized zinc on steel sheet and a steel base plate is advantageous for the same case. The reason for this selection is that, for this gauging, fluorescent X-rays from zinc are selected and detected, leaving fluorescent X-rays from the base steel, but prefect separation of these X-rays is impossible and the zinc X-ray zone includes some steel X-rays.

Aluminium foil is preferable for gauging the thickness of tin-plate sheet, because tin foil as thin as plate tin, approximately 50 $\mu$m thick, could not be obtained and because fluorescent X-rays from the base steel somewhat absorbed by tin in passing through the plated tin film are detected for thickness gauging, i.e. the absorption method is applied for gauging of tin-plate, and the thicker aluminium foil, which is easily obtainable, absorbs somewhat equivalent X-rays to plated tin.

Foil 1 has an even composition and is fixed to the base plate 2 by means of adhesion or the like. As illustrated in the drawing the base plate is rectangular and is of larger area than said foil so as to have a marginal portion not covered by said foil. Unevenness of the adhesion film does not give any influence on the accuracy of practical gauging. Precise parallelism of the foil upper surface to the base plate bottom surface is not required since a $\pm 3$ $\mu$m range of surface position shift in the normal direction thereof is allowed for usual thickness gauging. The foil may extend fully over the base plate without any bad effect.

What is claimed is:

1. A thickness standard sample adapted for calibration and adjustment of an X-ray fluorescence coating thickness gauge, comprising a flat metal base plate, a metal foil having a precise known even thickness less than the thickness of the base plate and receiving radiant rays, and means for adhesively securing said foil to said base plate.

2. A thickness standard sample as claimed in claim 1, wherein said base plate is made of steel and said foil is made of zinc.

3. A thickness standard sample as claimed in claim 1, wherein said foil is made of aluminium.

4. A thickness standard sample as claimed in claim 1, wherein said base plate is rectangular and of larger area than said foil, with a marginal portion not covered by said foil.

5. A method of calibrating an X-ray fluoescence coating thickness gauge which comprises providing a flat metal base plate, preparing a metal foil of known even thickness less than the thickness of said base plate, adhesively securing said foil to said base plate, irradiating said foil with X-rays while measuring the thickness of said foil with an X-ray thickness gauge and calibrating said gauge according to the known thickness of said foil.

6. A method according to claim 5, in which said base plate is made of steel and said foil is made of zinc.

7. A method according to claim 5, in which said foil is made of aluminum.

8. A method according to claim 5, in which said base plate is made rectangular and of larger area than said foil, said foil being positioned on said base plate so as to leave a marginal portion of said base plate not covered by said foil.

* * * * *